US008563054B2

(12) United States Patent
Miyake et al.

(10) Patent No.: US 8,563,054 B2
(45) Date of Patent: Oct. 22, 2013

(54) ANTI-INFLAMMATORY AGENT

(75) Inventors: Yasuo Miyake, Hiroshima (JP); Ito Yoko, Hiroshima (JP)

(73) Assignee: Maruzen Pharmaceuticals Co., Ltd., Hiroshima (JP)

(*) Notice: Subject to any disclaimer, the term of this patent is extended or adjusted under 35 U.S.C. 154(b) by 0 days.

(21) Appl. No.: 12/657,209

(22) Filed: Jan. 15, 2010

(65) Prior Publication Data

US 2010/0120903 A1 May 13, 2010

Related U.S. Application Data

(62) Division of application No. 11/886,270, filed as application No. PCT/JP2005/004562 on Mar. 15, 2005, now abandoned.

(51) Int. Cl.
*A61K 31/122* (2006.01)
*A61K 36/484* (2006.01)

(52) U.S. Cl.
USPC .................. 424/757; 514/545; 514/685

(58) Field of Classification Search
None
See application file for complete search history.

(56) References Cited

U.S. PATENT DOCUMENTS

| 5,985,935 | A | * | 11/1999 | Kharazmi et al. |
| 2003/0152588 | A1 | * | 8/2003 | Huang et al. |
| 2004/0121031 | A1 | | 6/2004 | Majeed et al. |
| 2004/0142049 | A1 | | 7/2004 | Mae et al. |
| 2005/0037042 | A1 | * | 2/2005 | Dieck et al. |

FOREIGN PATENT DOCUMENTS

| DE | 10224387 A1 * | 12/2003 |
| EP | 1 312 372 A1 | 5/2003 |
| JP | 56-138117 | 10/1981 |
| JP | 58-217583 | 12/1983 |
| JP | 59-046210 | 3/1984 |
| JP | 60-181022 | 9/1985 |
| JP | 01-149706 | 6/1989 |
| JP | 01-157909 | 6/1989 |
| JP | 01-311011 | 12/1989 |
| JP | 04-297418 | 10/1992 |
| JP | 05-070349 | 3/1993 |
| JP | 06-256151 | 9/1994 |
| JP | 07-010738 | 1/1995 |
| JP | 2001-163718 | 6/2001 |
| WO | 03/007974 | 1/2003 |

OTHER PUBLICATIONS

U**); http://www.beauty4skin.com/printer_eczema_dermatosis.shtml: Skin Care: Eczema and Dermatosis by Dermik Laboratories; Apr. 24, 2004. Downloaded from www on Sep. 21, 2012.*
Tsukiyama, R-I et al; Antimicrobial Agents and Chemotherapy, May 2002,; 46(5): 1226-1230. Antibacterial activity of Licochalcone A against spore-forming bacteria.*
Wang, Jiangguo et al., Application of active glycyrrhizic constituents to cosmetics, China Surfactant Detergent & Cosmetics, vol. 34, No. 4, pp. 249-251, Aug. 31, 2004.
Li, Hongzhu, The advancement of the study on licorice and its formulation, Foreign Medical Sciences: Traditional Chinese Medicine, vol. 22, No. 3, pp. 136-139 and 185, Dec. 31, 2000.
Anti-Inflammatory Properties of Licochalcone A from Glycyrrhiza Inflata on Various Human Skin Cells, Journal of the American Academy of Dermatology, C.V. Mosby, St. Louis, MO, US, vol. 52, No. 3, p. 97, Mar. 2005.
Shibata S. et al., Inhibitory Effects of Licochalcone A Isolated from Glycyrrhiza Inflata Root on Inflammatory Ear Edema and Tumour Promotion in Mice, Planta Medica, Thieme, Stuttgart, DE, vol. 57, No. 3, pp. 221-224, Jan. 1991.
Skin-Whitening Cosmetic Material, Preventing Pigmentation by UV—Contains Oil-Soluble Glycyrrhiza Extract, Ascorbic Acid (deriv.), Kojic Acid (deriv.), etc. and Antiinflammatory Agents, Derwent Host—Derwent, Jul. 1993.
Kang, Jong Soon et al., Glabridin, an Isoflavan from Licorice Root, Inhibits Inducible Nitric-Oxide Synthase Expression and Improves Survival of Mice in Experimental Model of Septic Shock, Journal of Pharmacology and Experimental Therapeutics, vol. 312, No. 3, pp. 1187-1194, Mar. 2005.
Tsukiyama, R-I et al., Antimicrobial Agents and Chemotherapy (May 2002), 46(5), 1226-1230, Antibacterial activity of licochalcone A against spore-forming bacteria.
Nakagawa, K et al. Biological & Pharmaceutical Bulletin, (Nov. 2004) vol. 27, No. 11, pp. 1775-1778., Licorice flavonoids suppress abdominal fat accumulation and increase in blood glucose level in obese diabetic KK-Ay mice. Abstract.
Yasuda, I et al. Tokyo-toritsu Eisei Kenkyusho Kenkyu Nenpo (1979), (30-1), 93-7. The evaluation of crude drugs. V. Quality of licorice root and its oriental medicinal preparations. Abstract.
http://www.herbdatanz.com/licorice_picture_monograph.htm Downloaded Sep. 27, 2008. "Glycyrrhiza", Licorice USD 1926. Glycyrrhiza. U.S. (Br.) Compiled by Ivor Hughes.
Yoshiyuki Kimura, (Effects of various components in Chinese and Japanese traditional medicine on arachidonatae metabolism, (J. Traditional Medicines), 1995, vol. 12, No. 1, pp. 10-23, abstract 3), Fig. 11, 12.
Yoshiyuki Kimura et al., Effects of Flavonoid Constituents in Licorice on Arachidonate Metabolism, (J. Traditional Medicines), 1987, vol. 4, No. 3, pp. 346-347.
Toshimitsu Kambara et al., New Dermatological Utility of Licorice Flavonoid Fraction-Effects on Comedo, (J. Society of Cosmetic Chemists of Japan), 2003, vol. 37, No. 3, pp. 179-186, Table 5.

(Continued)

*Primary Examiner* — Michele C. Flood
(74) *Attorney, Agent, or Firm* — Carmody & Torrance LLP

(57) ABSTRACT

An anti-inflammatory agent which includes an oil-soluble licorice extract, prepared by subjecting at least one of a leguminous plant of the genus *Glycyrrhiza* and a water extraction residue of a leguminous plant of the genus *Glycyrrhiza* to an extraction treatment with an organic solvent and which has at least one effect selected from an inhibitory effect on hyaluronidase activity, an inhibitory effect on hexosaminidase release (i.e., inhibitory effect on histamine release), an inhibitory effect on platelet aggregation, and an inhibitory effect on phospholipase $A_2$ activity.

7 Claims, No Drawings

(56) References Cited

OTHER PUBLICATIONS

Yokota, T. et al., The Inhibitory Effect of Glabridin from Licorice Extracts on Melanogenesis and Inflammation, Pigment Cell Research Supplement, Copenhagen, DK, vol. 11, pp. 355-361, Jan. 1998.

Tatsuhiko Tsutsumi et al., "Introduction to new functions of natural plant extracts and their application to cosmetics," Fragrance Journal, 2001, vol. 29, No. 1, pp. 93-96.

Rauchensteiner, F. et al; "Analysis and comparison of Radix Glycyrrhizae (licorice) from Europe and China by capillary-zone electrophoresis (CZE)," Journal of Pharmaceutical and Biomedical Analysis, vol. 38, No. 4, Jul. 15, 2005, pp. 594-600.

Fu, Y. et al., "Licochalcone-A, a novel flavonoid isolated from licorice root (*Glycyrrhiza glabra*), causes G2 and late-G1 arrests in androgen-independent PC-3 prostate cancer cells," Biomedical and Biophysical Research Communications, Academic Press Inc., vol. 322, No. 1, Sep. 10, 2004, pp. 263-270.

\* cited by examiner

ANTI-INFLAMMATORY AGENT

CROSS REFERENCE TO RELATED APPLICATIONS

This application is a divisional of U.S. application Ser. No. 11/886,270, which was filed on Feb. 26, 2008 now abandoned, which was the National Stage of International Application No. PCT/JP2005/004562, filed Mar. 15, 2005.

TECHNICAL FIELD

The present invention relates to an anti-inflammatory agent which contains an oil-soluble licorice extract, which has at least one effect selected from an inhibitory effect on hyaluronidase activity, an inhibitory effect on hexosaminidase release, an inhibitory effect on platelet aggregation, and an inhibitory effect on phospholipase $A_2$ activity, and which is suitably used especially as an external preparation for skin.

BACKGROUND ART

Licorice has been known as herbal medicine from long ago, and currently it is mainly used as raw material of a sweetener for food, medicines, quasi-drugs, etc. Among these, glycyrrhizin and glycyrrhetinic acid, a water extract of licorice, have excellent medicinal effects such as anti-inflammatory effect, antiulcer effect, and antiallergic effect, and are widely used in e.g. food and drink, medicines, and cosmetics.

Oil-soluble licorice extract, which is obtained by extracting licorice with an organic solvent such as ethanol and ethyl acetate, It is known to contain a lot of flavonoids other than the above-mentioned glycyrrhizin and glycyrrhetinic acid. It is disclosed that this oil-soluble licorice extract has useful effects such as an antioxidant effect (See, Patent Literature 1), an oxidation preventing effect (See, Patent Literature 2), a whitening effect (See, Patent Literatures 3 and 4), and an ultraviolet absorbing effect (See, Patent Literature 5).

However, it has not been known that the oil-soluble licorice extract has at least one effect selected from an inhibitory effect on hyaluronidase activity, an inhibitory effect on hexosaminidase release, an inhibitory effect on platelet aggregation, and an inhibitory effect on phospholipase $A_2$ activity, and is useful for, for example, contact dermatitis (rash), psoriasis, pemphigus vulgaris, and other various skin diseases associated with chapped skin.

Patent Literature 1: Japanese Patent Application Laid-Open (JP-A) No. 58-217583
Patent Literature 2: JP-A No. 59-46210
Patent Literature 3: JP-A No. 01-149706
Patent Literature 4: JP-A No. 01-311011
Patent Literature 5: JP-A No. 01-157909

DISCLOSURE OF INVENTION

Under such circumstances, the present invention has been achieved. An object of the present invention is to solve conventional problems mentioned above and to achieve the following objects. Specifically, an object of the present invention is to provide an anti-inflammatory agent that can prevent and improve inflammatory diseases through at least one effect selected from an inhibitory effect on hyaluronidase activity, an inhibitory effect on hexosaminidase release, an inhibitory effect on platelet aggregation, and an inhibitory effect on phospholipase $A_2$ activity.

Means for solving the above-mentioned problems are as follows.

<1> An anti-inflammatory agent including an oil-soluble licorice extract.

<2> The anti-inflammatory agent according to <1>, wherein the oil-soluble licorice extract is prepared by subjecting at least one of a leguminous plant of the genus *Glycyrrhiza* and a water extraction residue of a leguminous plant of the genus *Glycyrrhiza* to an extraction treatment.

<3> The anti-inflammatory agent according to one of <1> and <2>, wherein the anti-inflammatory agent is prepared by subjecting at least one of roots, rhizomes, leaves, and stems of a leguminous plant of the genus *Glycyrrhiza*, and water extraction residues thereof to an extraction treatment with an organic solvent.

<4> The anti-inflammatory agent according to <3>, wherein the organic solvent is at least one selected from ethanol, hydrous ethanol, and ethyl acetate.

<5> The anti-inflammatory agent according to any one of <2> to <4>, wherein the leguminous plant of the genus *Glycyrrhiza* is at lease one selected from *Glycyrrhiza glabra*, *Glycyrrhiza inflata*, *Glycyrrhiza araleasis*, *Glycyrrhiza uralensis*, and *Glycyrrhiza echinata*.

<6> The anti-inflammatory agent according to any one of <1> to <5>, wherein the oil-soluble licorice extract includes at least one flavonoid of glabridin and licochalcone A.

<7> The anti-inflammatory agent according to <6>, wherein a total content of the at least one flavonoid of glabridin and licochalcone A in the oil-soluble licorice extract is 1% by mass to 80% by mass based on dry solid content.

<8> The anti-inflammatory agent according to any one of <5> to <7>, wherein a content of glabridin in an oil-soluble licorice extract of *Glycyrrhiza glabra* is 1% by mass or more based on dry solid content.

<9> The anti-inflammatory agent according to any one of <5> to <8>, wherein a content of licochalcone A in an oil-soluble licorice extract of *Glycyrrhiza echinata* is 1% by mass or more based on dry solid content.

<10> The anti-inflammatory agent according to any one of <5> to <9>, wherein a content of licochalcone A in an oil-soluble licorice extract of *Glycyrrhiza inflata* is 1% by mass or more based on dry solid content.

<11> The anti-inflammatory agent according to any one of <1> to <10>, wherein the oil-soluble licorice extract has at least one effect selected from an inhibitory effect on hyaluronidase activity, an inhibitory effect on hexosaminidase release, an inhibitory effect on platelet aggregation, and an inhibitory effect on phospholipase $A_2$ activity.

<12> The anti-inflammatory agent according to any one, of <1> to <11>, which is used as an external preparation for skin.

The anti-inflammatory agent of the present invention includes an oil-soluble licorice extract, is prepared, particularly by subjecting at least one of a leguminous plant of the genus *Glycyrrhiza* and a water extraction residue of a leguminous plant of the genus *Glycyrrhiza* to an extraction treatment with an organic solvent, and, through an inhibitory effect on hyaluronidase activity, an inhibitory effect on hexosaminidase release (i.e., inhibitory effect on histamine release), an inhibitory effect on platelet aggregation, and an inhibitory effect on phospholipase $A_2$ activity, can attain efficient prevention and improvement of inflammations related to these.

In addition, the anti-inflammatory agent of the present invention is particularly suitably used for an external preparation for skin due to its excellent feel and high safety. Here, in the present invention, the "external preparation for skin"

means various drugs that are applied for skin and is a concept that include, for example, cosmetics, quasi-drugs, and medicines.

BEST MODE FOR CARRYING OUT THE INVENTION

The anti-inflammatory agent of the present invention contains an oil-soluble licorice extract and further contains additional components on as-needed basis.

The oil-soluble licorice extract is not particularly limited and can be appropriately selected depending on the application, but oil-soluble licorice extracts are suitable that are prepared by subjecting at least one of a leguminous plant of the genus *Glycyrrhiza* and a water extraction residue of a leguminous plant of the genus *Glycyrrhiza* to an extraction treatment with an organic solvent.

The leguminous plant of the genus *Glycyrrhiza* is not particularly limited and can be appropriately selected depending on the intended active ingredient. Examples thereof include *Glycyrrhiza glabra, Glycyrrhiza inflata, Glycyrrhiza araleasis, Glycyrrhiza uralensis, Glycyrrhiza echinata*, and the like. Among these, *Glycyrrhiza glabra, Glycyrrhiza echinata*, and *Glycyrrhiza inflata* are particularly preferable.

Licorice is often called with the name of the place of production, for example, licorice of northeast and northwest China (*Glycyrrhiza uralensis*), Sinkiang licorice or Shinkyo kanzoh in Japanese (*Glycyrrhiza echinata*), Russian licorice (*Glycyrrhiza glabra*), Spanish licorice (*Glycyrrhiza echinata*), Mongolian licorice, and Afghan licorice.

Any site of roots, rhizomes, leaves, and stems of the above-mentioned licorice can be used as a raw material for the extraction of the oil-soluble licorice extract. However, at least one of roots and rhizomes are particularly preferable in that the content of flavonoid such as glabridin and licochalcone A is high. Although the raw materials may be used for extraction as it is or may be used for extraction after drying, but dried roots and dried rhizomes are particularly preferable.

A water extraction residue of the raw material for extraction, i.e., a water extraction residue of the above-mentioned licorice, can also be used as a raw material for the extraction of the oil-soluble licorice extract.

The water extraction residue of licorice means a solid residue after extraction of licorice with at least one of water, warm water, and hot water, and neutral or weak alkaline cold water, warm water, and hot water in order to obtain glycyrrhizin and the like from the licorice. The residue after water extraction may contain water or may be dried.

Use of water extraction residue of licorice as a raw material for extraction as mentioned above has an advantage that water extraction residue of licorice can be utilized efficiently, improving productivity.

The organic solvent is not particularly limited and can be appropriately selected depending on the application. Examples thereof include benzene, toluene, xylene, ethyl ether, methyl ethyl ketone, methyl isobutyl ketone, dichloromethane, dichloroethane, chloroform, ethyl acetate, propyl acetate, butyl acetate, acetone, methanol, ethanol, propanol, hydrous methanol, hydrous ethanol, hydrous propanol, and the like. Further, carbon dioxide can also be used as a supercritical fluid. Among these organic solvents, ethanol, hydrous ethanol, and ethyl acetate are preferably used in terms of safety. For the hydrous ethanol, those with an ethanol concentration of 30% by mass to 99% by mass are suitable.

The condition of extraction for obtaining oily extracts of licorice from the licorice or water extraction residues of licorice with use of the organic solvent is not particularly limited and can be appropriately selected depending on the application. For example, 2- to 15-fold amount of organic solvent based on raw material for extraction is added, and extracted with stirring at room temperature or extracted by heating. In addition, repeated operation of these methods singly or in combination is more preferable since extraction efficiency is improved.

The obtained extract is subjected to centrifugation and filtration, by which insoluble matter is removed. The resulting solution can be used as an oil-soluble licorice extract without further treatment, or after further treatment where the resulting solution is concentrated in the usual manner. In addition, deodorization, decoloration, and the like may be performed appropriately unless the intended physiological effect is impaired. For this deodorization and decoloration, an activated carbon, synthetic adsorbent resin, ion-exchange resin, and the like are typically used. By drying extract by an appropriate method, yellowish brown extract powder can be obtained as an oil-soluble licorice extract.

The obtained liquid extracts without further treatment, or those obtained after concentration of liquid extracts, and dry powder of or dry solid of liquid extracts are utilized as an oil-soluble licorice extract.

Flavonoid can be purified from the oil-soluble licorice extract by any method without limitation, and the purification method can be appropriately selected from known methods for purifying an organic compound depending on the application. For example, purification can be performed by treating the oil-soluble licorice extract by means of one of normal phase silica gel chromatography and reverse phase chromatography, and then crystallizing from acetone. By this method, pure product of active ingredient can be obtained relatively easily. Other purification methods include column chromatography using a synthetic adsorbent such as Diaion HP-20 (manufactured by Mitsubishi Chemical Corporation), liquid-liquid countercurrent partition, and the like.

The flavonoid that is contained in the oil-soluble licorice extract is different depending on the species of licorice, which is a raw material for extraction, so that it is impossible to define definitely. However, examples of the flavonoid include glabridin, glabrene, licochalcone A, licochalcone B, glycycoumarin, glisoflavone and the like. Among these, glabridin, glabrene, licochalcone A, and licochalcone B are particularly preferable, and glabridin and licochalcone A are most preferable since they have a high anti-inflammatory effect.

The total content of at least one flavonoid of the glabridin and licochalcone A in the oil-soluble licorice extract is preferably 1% by mass to 80% by mass, and more preferably 5% by mass to 60% by mass, based on dry solid content.

The content of glabridin in the oil-soluble licorice extract of the *Glycyrrhiza glabra* is preferably 1% by mass or more, more preferably 10% by mass or more, and still more preferably 20% by mass to 50% by mass, based on dry solid content.

The content of licochalcone A in the oil-soluble licorice extract of the *Glycyrrhiza echinata* is preferably 1% by mass or more, more preferably 5% by mass or more, and still more preferably 10% by mass to 40% by mass, based on dry solid content.

The content of licochalcone A in the oil-soluble licorice extract of the *Glycyrrhiza inflata* is preferably 1% by mass or more, more preferably 5% by mass or more, and still more preferably 10% by mass to 40% by mass, based on dry solid content.

The anti-inflammatory agent of the present invention can prevent and improve various inflammatory diseases including skin diseases such as contact dermatitis (rash), psoriasis and pemphigus vulgaris through at least one effect selected from an inhibitory effect on hyaluronidase activity, an inhibitory effect on hexosaminidase release, (i.e., inhibitory effect on histamine release), an inhibitory effect on platelet aggregation, and an inhibitory effect on phospholipase $A_2$ activity.

Here, the hyaluronidase is a hyaluronan hydrolase and exists in a mast cell, and it is said that the hyaluronidase is involved in degranulation of mast cell through its activation. Thus, by inhibiting the activation of hyaluronidase, stabilization of hyaluronan can be attained, release of various chemical mediators from a mast cell can be prevented, and enhancement of moisture retention or anti-inflammatory effect can be expected.

In addition, since hexosaminidase is also released simultaneously upon release of histamine inside a cell, the inhibitory effect on histamine release can be evaluated using hexosaminidase release as an indicator of histamine release. The histamine is present in a mast cell, and when the mast cell is stimulated, it is released by degranulation reaction and acts as prophlogistic or inflammation-causing substance and as an allergenic substance. The histamine released from activated mast cell causes increased vascular permeability, smooth muscle contraction, increased mucus secretion, etc., resulting in allergic diseases such as bronchial asthma, allergic rhinitis, and urticaria. Therefore, inhibition of release of hexosaminidase, i.e., inhibition of release of histamine enables prevention and treatment of allergic diseases and inflammatory diseases.

The platelet aggregation invites activation of phospholipase $A_2$ in the arachidonate cascade, thereby leukotriene B, prostaglandin $E_2$, and the like are released, and these substances cause inflammation. Thus, allergic diseases and inflammatory diseases can be prevented and treated by substances that inhibit aggregation of platelet.

The phospholipase $A_2$ is an important enzyme in the arachidonate cascade, which is a metabolic pathway of arachidonic acid, and excessive activation of phospholipase $A_2$ leads to abnormal metabolism of arachidonic acid, causing inflammation, allergy, asthma, ischemia, myocardial infarction, etc. Therefore, by inhibiting the activation of phospholipase $A_2$, allergic diseases and inflammatory diseases can be prevented and treated.

The anti-inflammatory agent of the present invention is not particularly limited and can be appropriately selected depending on the application, but it is suitably used as an external preparation for skin. The external preparation for skin means various drugs that are applied for skin, including, for example, cosmetics, quasi-drugs, and medicines. Examples of the external preparation for skin include ointment, cream, milky lotion, lotion, pack, jelly, lip cream, lipstick, bath agent, tonic, rinse, shampoo, astringent, and the like.

The amount of the anti-inflammatory agent to be mixed or compounded in the external preparation for skin can be appropriately adjusted depending on the type of the external preparation for skin, bioactivity of extract, etc., but is preferably 0.001% by mass to 10% by mass and more preferably 0.01% by mass to 5% by mass.

The anti-inflammatory agent of the present invention, described above, is suitably applied to humans, but is also applied to animals other than humans as long as each effect is achieved.

Hereafter, the present invention will be described in detail by means of examples, but it will be understood that the present invention should not be construed as being limited thereby.

Production Example 1

Preparation of Oil-Soluble Licorice Extract

10 L of dehydrated ethanol was added to 1 kg of licorice (*Glycyrrhiza glabra* Linne var. *glandulifera* Regel et Herder) root and extraction was performed for 5 hours under reflux. The obtained extract was subjected to vacuum concentration. To this concentrated extract, was added 1 L of ethyl acetate, extracted for 5 hours under reflux, subjected to vacuum drying, and then grinded to prepare 10 g of oil-soluble licorice extract.

The content of flavonoid in the prepared oil-soluble licorice extract of Production Example 1 was determined quantitatively using high-performance liquid chromatography (manufactured by JASCO Corporation). The prepared oil-soluble licorice extract of Production Example 1 contained 20% by mass of glabridin.

Production Example 2

Preparation of Oil-Soluble Licorice Extract

10 L of dehydrated ethanol was added to 1 kg of licorice (*Glycyrrhiza glabra* Linne var. *glandulifera* Regel et Herder) root and extraction was performed for 5 hours under reflux. The obtained extract was subjected to vacuum concentration. To this concentrated extract, was added 1 L of ethyl acetate and extraction was performed for 5 hours under reflux. This was roughly purified with a synthetic adsorbent (manufactured by Mitsubishi Chemical Corporation), subjected to vacuum drying, and then grinded to prepare 5 g of oil-soluble licorice extract.

The content of flavonoid in the prepared oil-soluble licorice extract of Production Example 2 was determined quantitatively using high-performance liquid chromatography (manufactured by JASCO Corporation). The prepared oil-soluble licorice extract of Production Example 2 contained 40% by mass of glabridin.

Production Example 3

Preparation of Oil-Soluble Licorice Extract

10 L of dehydrated ethanol was added to 1 kg of licorice (*Glycyrrhiza inflata* Batalin) root and extraction was performed for 5 hours under reflux. The obtained extract was subjected to vacuum concentration. To this concentrated extract, was added 1 L of ethyl acetate and extraction was performed for 5 hours under reflux. The obtained extract was subjected to vacuum concentration. To this concentrated extract, was added 1 L of ethyl acetate, extracted for 5 hours under reflux, subjected to vacuum drying, and then grinded to prepare 30 g of oil-soluble licorice extract.

The content of flavonoid in the prepared oil-soluble licorice extract of Production Example 3 was determined quantitatively using high-performance liquid chromatography (manufactured by JASCO Corporation). The prepared oil-soluble licorice extract of Production Example 3 contained 20% by mass of licochalcone A.

Production Example 4

Purification of Glabridin 20 g of oil-soluble licorice extract prepared in Production Example 2 was dissolved in chloroform, mixed with silica gel (silica gel 60, manufactured by Merck Ltd.), and then dried. This dried material was deposited or loaded on a column packed with 1 kg of silica gel the same as that mentioned above and eluted with a chloroform/methanol mixture (30:1). The fraction containing glabridin was collected. The solvent of this fraction was evaporated away under reduced pressure to obtain 5.8 g of solid. Next, the obtained solid was dissolved in a small amount of methanol, mixed with reversed-phase silica gel (ODS DM1020T, manufactured by Fuji Silysia Chemical Ltd.), dried, and deposited or loaded on a column which was packed with 800 g of reversed-phase silica gel previously. A methanol/water mixture (60:40) was passed through this column as an elution solvent, and the fraction containing glabridin was collected. The solvent was distilled away from this fraction under reduced pressure. The obtained solid (4.3 g) was dissolved in 40 ml of acetone and left at rest at 5° C. for 3 days to obtain 3.8 g of crystalline glabridin.

Production Example 5

Purification of Licochalcone A 120 g of oil-soluble licorice extract prepared in Production Example 3 was dissolved in chloroform, mixed with silica gel (silica gel 60, manufactured by Merck Ltd.), and then dried. This dried material was deposited or loaded on a column packed with 3 kg of silica gel the same as that mentioned above and eluted with an n-hexane/ethyl acetate mixture (2:1). The fraction containing licochalcone A was collected. The solvent of this fraction was evaporated away under reduced pressure to obtain 50 g of solid. Then, the obtained solid was dissolved in a small amount of methanol, mixed with reversed-phase silica gel (ODS DM1020T, manufactured by Fuji Silysia Chemical Ltd.), dried, and deposited or loaded on a column which was packed with reversed-phase silica gel previously. A methanol/water mixture (60:40) was passed through this column as an elution solvent, and the fraction containing licochalcone A was collected. The solvent was evaporated away from this fraction under reduced pressure. The obtained solid (25 g) was dissolved in a methanol/water mixture (70:30) and left at rest at room temperature for 1 day to obtain 15.2 g of crystalline licochalcone A.

Example 1

Hyaluronidase Activity Inhibition Assay

For the extracts and purified materials prepared in Production Examples 1 to 5 (hereinafter, may be referred to as "sample"), inhibitory effect on hyaluronidase activity was tested as follows.

First, 0.1 mL of hyaluronidase solution (Type IV-S (from bovine testis; SIGMA 400 NF units/mL) was added to 0.1 mol/L acetic acid buffer (pH 3.5) in which each sample was dissolved, and allowed to react at 37° C. for 20 minutes.

Next, 0.2 mL of 2.5 mmol/L calcium chloride was added as an activating agent and allowed to react at 37° C. for 20 minutes. To this solution, 0.5 mL of 0.4 mg/mL potassium hyaluronate solution (from rooster comb) was added and allowed to react at 37° C. for 40 minutes. After that, reaction was stopped by adding 0.2 mL of 0.4 mol/L sodium hydroxide and cooled. Then, 0.2 mL of boric acid solution was added to each reaction solution and boiled for 3 minutes. After cooling on ice, 6 mL of p-dimethyl aminobenzaldehyde (p-DABA) reagent was added and allowed to react at 37° C. for 20 minutes. After that, absorbance at the wavelength of 585 nm was determined.

Next, similar operations and absorbance determination were performed without addition of enzyme. Further, as a control, using distilled water instead of sample solution, similar operations and absorbance determination were performed.

From the results of the measurements mentioned above, the percentage inhibition of hyaluronidase activity was calculated according to the following formula 1:

% Inhibition of hyaluronidase activity=[1−($St$−$Sb$)/($Ct$−$Cb$)]×100    <Formula 1> where St represents the absorbance at the wavelength of 585 nm of the sample solution; Sb represents the absorbance at the wavelength of 585 nm of the sample solution blank; Ct represents the absorbance at the wavelength of 585 nm of the control solution; and Cb represents the absorbance at the wavelength of 585 nm of the control solution blank.

Next, the sample concentration was reduced in a stepwise manner, and the above-mentioned percentage inhibition of hyaluronidase activity was measured. The sample concentration, at which 50% of hyaluronidase activity is inhibited, was determined by interpolation. The results are shown in Table 1. The smaller this value is, the stronger the inhibitory effect on hyaluronidase activity is.

TABLE 1

| | Sample concentration for 50% inhibition of hyaluronidase activity |
|---|---|
| Oil-Soluble Licorice Extract of Production Example 1 | 189.4 μg/ml |
| Oil-Soluble Licorice Extract of Production Example 2 | 54.5 μg/ml |
| Oil-Soluble Licorice Extract of Production Example 3 | 14.6% (when 400 μg/ml was added) |
| Glabridin of Production Example 4 | 18.3 μg/ml |
| Licochalcone A of Production Example 5 | 17.2 μg/ml |

From the results of Table 1, it was confirmed that oil-soluble licorice extracts of Production Examples 1 to 3, glabridin of Production Example 4, and licochalcone A of Production Example 5 have an inhibitory effect on hyaluronidase activity.

Example 2

Assay of Inhibitory Effect on Hexosaminidase Release

For the extracts and purified materials prepared in Production Examples 1 to 5 (hereinafter, may be referred to as "sample"), inhibitory effect on hexosaminidase release was tested as follows. Since hexosaminidase is also released simultaneously upon release of to histamine inside a cell, the inhibitory effect on histamine release can be evaluated using hexosaminidase release as an indicator of histamine release.

First, rat basophilic leukemia cells (RBL-2H3) were cultured using a medium (S-MEM medium with 15% FBS; hereinafter the same) placed in 25 mL culture flasks, and then cells were collected by trypsin treatment. The collected cells were diluted with S-MEM medium to a concentration of $4.0 \times 10^5$ cells/mL, and mouse monoclonal anti-dinitrophenyl group IgE (DNP-specific-IgE) was added to a final concentration of 0.5 μg/mL. Then, 100 μl of this cell suspension was seeded in a well of a 96-well plate and cultured overnight.

After cultivation, S-MEM medium was removed, and washed twice with 500 μL of Siraganian buffer.

Next, 30 μL of Siraganian buffer and 10 μL of each sample, prepared using Siraganian buffer, were added and left at rest at 37° C. for 10 minutes. After that, 10 μL of 100 ng/mL dinitrophenylated bovine serum albumin (DNP-BSA) was added and left at rest at 37° C. for 15 minutes to release hexosaminidase.

Then, release was stopped by leaving the 96 well plate at rest on ice. 110 μL of cell supernatant of each well and 10 μL of 1 mmol/L p-nitrophenyl-N-acetyl-β-D-glucosaminide (p-NAG) solution were added to a fresh 96 well plate and allowed to react at 37° C. for 1 hour. After completion of the reaction, 250 μL of 0.1 mol/L $Na_2CO_3$/$NaHCO_3$ was added to each well, and the absorbance at the wavelength of 415 nm was determined.

Next, as a blank test, the absorbance of a mixture of 10 μl it of cell supernatant and 250 μL of 0.1 mol/L $Na_2CO_3$/$NaHCO_3$ at the wavelength of 415 nm was determined and was used for correction.

From the results of the measurements mentioned above, the percentage inhibition of hexosaminidase release was determined according to the following formula 2:

$$\% \text{ Inhibition of hexosaminidase release} = [1-(B-C)/A] \times 100 \quad <\text{Formula 2}>$$

where A represents the absorbance at the wavelength of 415 nm without the addition of sample; B represents the absorbance at the wavelength of 415 nm with the addition of sample; and C represents the absorbance at the wavelength of 415 nm with the addition of sample and without the addition of p-NAG.

Next, the sample concentration was reduced in a stepwise manner, and the above-mentioned percentage inhibition of hexosaminidase release was measured. The sample concentration, at which 50% of release of hexosaminidase is inhibited, was determined by interpolation. The results are shown in Table 2. The smaller this value is, the stronger the inhibitory effect on hexosaminidase release is.

TABLE 2

|  | Sample concentration for 50% inhibition of hexosaminidase release |
|---|---|
| Oil-Soluble Licorice Extract of Production Example 1 | 19.1 μg/ml |
| Oil-Soluble Licorice Extract of Production Example 2 | 18.6% (when 10 ppm was added) |
| Oil-Soluble Licorice Extract of Production Example 3 | 17.0 μg/ml |
| Glabridin of Production Example 4 | — |
| Licochalcone A of Production Example 5 | 23.5 μg/ml |

From the results of Table 2, it was confirmed that oil-soluble licorice extracts of Production Examples 1 to 3, and licochalcone A of Production Example 5 have an inhibitory effect on hexosaminidase release (i.e., inhibitory effect on histamine release).

Example 3

Platelet Aggregation Inhibitory Effect

For the extracts and purified materials prepared in Production Examples 1 to 5 (hereinafter, may be referred to as "sample"), inhibitory effect on platelet aggregation was tested as follows.

First, rabbit blood, which was collected with the addition of ¹/₁₀ amount of 77 mmol/L EDTA (pH 7.4), was centrifuged (180×g, 10 minutes, room temperature) to obtain platelet suspension. Next, the platelet suspension was centrifuged (810×g, 10 minutes, 4° C.), and the supernatant was removed to obtain platelet. This was suspended in platelet washing solution (0.15 mol/L sodium chloride: 0.15 mol/L Tris-HCL buffer (pH 7.4): 77 mmol/L EDTA (pH7.4)=90:8:2), centrifuged in the same way as mentioned above. The obtained platelet was suspended in platelet suspension (10 mmol/L HEPES buffer (pH 7.4) containing 145 mmol/L sodium chloride, 5 mmol/L potassium chloride and 5.5 mmol/L glucose), and thereby the number of platelet was adjusted ($3.0 \times 10^5$ cells/μL) to prepare washed platelet suspension.

Next, to 222 μL of the prepared washed platelet suspension, 1 μL of 200 mmol/L calcium chloride solution was added and allowed to react at 37° C. for 1 minute. To this solution, 2 μL of each sample was added and further allowed to react for 2 minutes. A stirring bar was placed, the solution was stirred for 1 minute, and then 25 μL of 10 ppm collagen solution was added as an aggregation inducing agent. Rate of platelet aggregation at 37° C. for 10 minutes was measured with a platelet aggregation measuring device (PAM12CL, manufactured by Mebanics Inc.), and the percentage inhibition of platelet aggregation was determined according to the following formula 3. Separately, rate of platelet aggregation, B, was determined in a similar operation to that mentioned above except that the solvent of sample solution was added instead of the sample solution.

$$\% \text{ Inhibition of platelet aggregation} = [(B-A)/B] \times 100 \quad <\text{Formula 3}>$$

where A represents the rate of platelet aggregation when an aggregation inducing agent and a sample solution were added; and B represents the rate of platelet aggregation when an aggregation inducing agent was added and a sample solution was not added.

Next, the sample concentration was reduced in a stepwise manner, and the above-mentioned percentage inhibition of platelet aggregation was measured. The sample concentration, at which 50% of platelet aggregation is inhibited, was determined by interpolation. The results are shown in Table 3. The smaller this value is, the stronger the inhibitory effect on platelet aggregation is.

TABLE 3

|  | Sample concentration for 50% inhibition of platelet aggregation |
|---|---|
| Oil-Soluble Licorice Extract of Production Example 1 | 2.0 μg/ml |
| Oil-Soluble Licorice Extract of Production Example 2 | 4.3 μg/ml |
| Oil-Soluble Licorice Extract of Production Example 3 | 0.38 μg/ml |
| Glabridin of Production Example 4 | 400 μg/ml |
| Licochalcone A of Production Example 5 | 79.7 μg/ml |

From the results of Table 3, it was confirmed that oil-soluble licorice extracts of Production. Examples 1 to 3, glabridin of Production Example 4, and licochalcone A of Production Example 5 have an inhibitory effect on platelet aggregation.

Example 4

Phospholipase $A_2$ Activity Inhibitory Effect

For the extracts and purified materials prepared in Production Examples 1 to 5 (hereinafter, may be referred to as "sample"), inhibitory effect on phospholipase $A_2$ activity was tested as follows.

First, rat leukemia cells, RBL-2H3 cells, were cultured in a MEM medium containing 15 v/v % FBS in 75 cm² flasks at 37° C. under 5% $CO_2$-95% air, and cells were collected in the usual manner. The collected cells were adjusted using a MEM medium containing 15 v/v % FBS to $5×10^5$ cells/mL. Further, [$^3$H] arachidonic acid (50 µCi/500 µL) was added to a concentration of 3 µL/10 mL. 1 mL of the prepared solution was seeded in a 24-well plate and cultured overnight at 37° C. under 5% $CO_2$ 95% air. The medium in each well was discarded, washed with PBS (−), followed by the addition of serum free MEM medium, and incubated at 37° C. for 30 minutes.

Next, a solution, in which sample was dissolved, was added to each well and incubated for 10 minutes in the same way. Further, 10 of 1 mmol/L A23187 (manufactured by Sigma-Aldrich) was added and incubated at 37° C. for 5 minutes. After the reaction, 500 µL of supernatant was taken under water cooling, 6 mL of scintillation cocktail was added, and radioactivity was measured in a liquid scintillation counter.

Next, in the same manner, radioactivity was measured for a blank test (without A23187 stimulation) and for a control (solvent of sample solution).

From the results of the measurements obtained, the percentage inhibition of phospholipase $A_2$ activity was determined according to the following formula 4:

$$\text{\% Inhibition of phospholipase } A_2 \text{ activity} = [(B-A)/(B-C)] \times 100 \quad \text{<Formula 4>}$$

where A represents the radioactivity when sample was added; B represents the radioactivity of control; and C represents the radioactivity of blank test.

Next, the sample concentration was reduced in a stepwise manner, and the above-mentioned percentage inhibition of phospholipase $A_2$ activity was measured. The sample concentration, at which 50% of phospholipase $A_2$ activity is inhibited, was determined by interpolation. The results are shown in Table 4. The smaller this value is, the stronger the inhibitory effect on phospholipase $A_2$ activity.

TABLE 4

| | Sample concentration for 50% inhibition of phospholipase $A_2$ activity |
|---|---|
| Oil-Soluble Licorice Extract of Production Example 1 | 3.7 µg/ml |
| Oil-Soluble Licorice Extract of Production Example 2 | 1.5 µg/ml |
| Oil-Soluble Licorice Extract of Production Example 3 | 0.4 µg/ml |
| Glabridin of Production Example 4 | — |
| Licochalcone A of Production Example 5 | — |

From the results of Table 4, it was confirmed that oil-soluble licorice extracts of Production Examples 1 to 3 have an inhibitory effect on phospholipase $A_2$ activity.

Compounding Example 1

A cream with anti-inflammatory effect that has the following composition was produced by a conventional method.

| | |
|---|---|
| Liquid paraffin | 5.0 g |
| White beeswax | 4.0 g |
| Cetanol | 3.0 g |
| Squalane | 10.0 g |
| Lanolin | 2.0 g |
| Stearic acid | 1.0 g |
| Polyoxyethylene sorbitan oleate (20 E. O) | 1.5 g |
| Glyceryl monostearate | 3.0 g |
| 1,3-Butylene glycol | 6.0 g |
| Methyl parahydroxybenzoate | 1.5 g |
| Perfume | 0.1 g |
| Oil-soluble licorice extract of Production Example 1 | 0.01 g |
| Purified water | balance |
| Total | 100 g |

Compounding Example 2

A milky lotion with anti-inflammatory effect that has the following composition was produced by a conventional method.

| | |
|---|---|
| Jojoba oil | 4.0 g |
| Placenta extract | 0.1 g |
| Olive oil | 2.0 g |
| Squalane | 2.0 g |
| Cetanol | 2.0 g |
| Glyceryl monostearate | 2.0 g |
| Polyoxyethylene cetyl ether (20 E. O) | 2.5 g |
| Polyoxyethylene sorbitan oleate (20 E. O) | 2.0 g |
| 1,3-Butylene glycol | 3.0 g |
| Hinokitiol | 0.15 g |
| Perfume | 0.05 g |
| Oil-soluble licorice extract of Production Example 2 | 0.01 g |
| Purified water | balance |
| Total | 100 g |

Compounding Example 3

A pack with anti-inflammatory effect that has the following composition was produced by a conventional method.

| | |
|---|---|
| Polyvinyl alcohol | 15 g |
| Polyethylene glycol | 3 g |
| Propylene glycol | 7 g |
| Ethanol | 10 g |
| Ethyl parahydroxybenzoate | 0.05 g |
| Perfume | 0.05 g |
| Oil-soluble licorice extract of Production Example 3 | 0.05 g |
| Purified water | balance |
| Total | 100 g |

Compounding Example 4

A cream with anti-inflammatory effect that has the following composition was produced by a conventional method.

| | |
|---|---|
| Liquid paraffin | 5.0 g |
| White beeswax | 4.0 g |
| Cetanol | 3.0 g |
| Squalane | 10.0 g |

| | |
|---|---|
| Lanolin | 2.0 g |
| Stearic acid | 1.0 g |
| Polyoxyethylene sorbitan oleate (20 E. O) | 1.5 g |
| Glyceryl monostearate | 3.0 g |
| 1,3-Butylene glycol | 6.0 g |
| Methyl Parahydroxybenzoate | 1.5 g |
| Perfume | 0.1 g |
| Glabridin of Production Example 4 | 0.01 g |
| Purified water | balance |
| Total | 100 g |

Compounding Example 5

A pack with anti-inflammatory effect that has the following composition was produced by a conventional method.

| | |
|---|---|
| Polyvinyl alcohol | 15 g |
| Polyethylene glycol | 3 g |
| Propylene Glycol | 7 g |
| Ethanol | 10 g |
| Ethyl parahydroxybenzoate | 0.05 g |
| Perfume | 0.05 g |
| Licochalcone A of Production Example 5 | 0.05 g |
| Purified water | balance |
| Total | 100 g |

INDUSTRIAL APPLICABILITY

The anti-inflammatory agent of the present invention is prepared by subjecting at least one of a leguminous plant of the genus *Glycyrrhiza* and a water extraction residue of a leguminous plant of the genus *Glycyrrhiza* to an extraction treatment with an organic solvent, has at least one effect selected from an inhibitory effect on hyaluronidase activity, an inhibitory effect on hexosaminidase release, an inhibitory effect on platelet aggregation, and an inhibitory effect on phospholipase $A_2$ activity, and is suitably used especially as a skin cosmetic such as skin toner, cream, milky lotion, lotion, and pack.

The invention claimed is:

1. A method for inhibiting hyaluronidase activity, comprising administering an agent comprising a therapeutically effective amount of licochalcone A to a person in need of inhibiting hyaluronidase activity in the person's body to inhibit hyaluronidase activity in the person's body;
    wherein the person in need of inhibiting hyaluronidase activity in the person's body is a person having pemphigus vulgaris.

2. The method according to claim 1, wherein the agent is prepared by subjecting at least one of (i) a leguminous plant of the genus *Glycyrrhiza* and (ii) a water extraction residue of a leguminous plant of the genus *Glycyrrhiza*, to an extraction treatment.

3. The method according to claim 1, wherein the agent is prepared by subjecting at least one of (i) roots, rhizomes, leaves, and stems of a leguminous plant of the genus *Glycyrrhiza*, and (ii) water extraction residues thereof, to an extraction treatment with an organic solvent.

4. The method according to claim 3, wherein the organic solvent is at least one selected from ethanol, hydrous ethanol, and ethyl acetate.

5. The method according to claim 2, wherein the leguminous plant of the genus *Glycyrrhiza* is at least one selected from *Glycyrrhiza inflata*, and *Glycyrrhiza echinata*.

6. The method according to claim 1, wherein the administering of the agent is by applying the agent to the skin of the person in need of inhibiting hyaluronidase activity in the person's body.

7. The method according to claim 1, wherein the inhibiting of the hyaluronidase activity release of chemical mediators from a mast cell.

* * * * *

UNITED STATES PATENT AND TRADEMARK OFFICE
CERTIFICATE OF CORRECTION

PATENT NO. : 8,563,054 B2  
APPLICATION NO. : 12/657209  
DATED : October 22, 2013  
INVENTOR(S) : Yasuo Miyake et al.

Page 1 of 1

It is certified that error appears in the above-identified patent and that said Letters Patent is hereby corrected as shown below:

In the Claims

Column 14, Line 36, Claim 7,

Delete "hyaluronidase activity release" and replace it with -- hyaluronidase activity inhibits release --

Signed and Sealed this
Fourth Day of February, 2014

Michelle K. Lee
*Deputy Director of the United States Patent and Trademark Office*